United States Patent [19]
Andrieux et al.

[11] Patent Number: 5,194,614
[45] Date of Patent: Mar. 16, 1993

[54] COMPOUNDS HAVING A NAPHTHALENE STRUCTURE

[75] Inventors: Jean Andrieux, Antony; Raymond Houssin, Marcq en Baroeul; Said Yous, Lille; Béatrice Guardiola, Neuilly sur Seine; Daniel Lesieur, Gondecourt, all of France

[73] Assignee: Adir et Compagnie, Courbevoie, France

[21] Appl. No.: 661,425

[22] Filed: Feb. 26, 1991

[30] Foreign Application Priority Data

Feb. 27, 1990 [FR] France .................. 90 02393

[51] Int. Cl.$^5$ .............. C07D 24/04; C07D 265/28; C07D 241/46; A61K 31/495; A61K 31/40
[52] U.S. Cl. .................. 544/400; 544/162; 544/355; 546/243; 546/262; 549/72; 548/543; 548/492; 548/952
[58] Field of Search .............. 544/162, 400, 355; 548/492, 543, 952; 546/243, 262; 549/72; 514/231.2, 255, 234.8, 351, 354, 419, 448

[56] References Cited

U.S. PATENT DOCUMENTS 3,259,622  7/1966  Shen et al. .................. 548/494
3,947,446  3/1976  Witte et al. .................. 544/398

FOREIGN PATENT DOCUMENTS 0113033 10/1978 Japan .................. 548/494

Primary Examiner—David B. Springer
Attorney, Agent, or Firm—Gordon W. Hueschen

[57] ABSTRACT

Compounds of general formula:

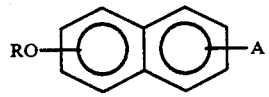

(I)

in which A and R are defined in the description.

11 Claims, No Drawings

COMPOUNDS HAVING A NAPHTHALENE STRUCTURE

The present invention concerns new compounds of 1-alkoxy-(2-acylaminoethyl)naphthalenes, a process for preparing these and pharmaceutical compositions containing them.

A certain number of (2-aminoethyl)naphthalenes have been described previously. Patent Application JP 50-089352 describes naphthalene derivatives having antipyretic, anti-inflammatory and analgesic activity. Patent Application JP 61-282348 describes (arylalkylamino-alkyl)naphthalenes as fungicidal agents. U.S. Pat. No. 4,327,022 describes aminoalkyldialkoxy-naphthalenes as fungicides. Patent Application EP 149,588 describes (hydroxyaminoalkyl)-methoxynaphthalenes as inhibitors of lipoxygenase and therefore useful for treating asthma, inflammation and psoriasis. Patent Application FR 70.44709describes 1-phenyl-2-[2-naphth-1-yl)ethylamino]ethanols as anti-spasmodics and vasodilators.

The applicant company has now discovered that new derivatives of 1-alkoxy-(2-acylaminoethyl)naphthalenes possess valuable pharmacological properties with regard to the central nervous system, particularly anxiolytic, antipsychotic and analgesic properties, and with regard to ovulation, cerebral circulation, immunomodulation, and are clearly distinguished from the aminoalkylnaphthalene compounds described above.

The subject of the invention is, more especially, the compounds of general formula (I):

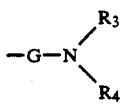

(I)

in which
A represents a

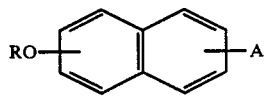

group,
R represents a linear or branched lower alkyl group,
R₁ represents a hydrogen atom or a linear or branched lower alkyl group, and
R₂ represents a hydrogen atom,
a linear or branched lower alkyl group or a cycloalkyl group optionally substituted by a halogen atom,
an aryl or heteroaryl or lower arylalkyl or substituted aryl or substituted heteroaryl or substituted arylalkyl group, it being understood that by heteroaryl group is understood an unsaturated mono- or bicyclic group including 1 to 3 heteroatoms chosen from among nitrogen, oxygen or sulfur, with each ring comprising 4 or 5 apexes, and that by aryl group is understood phenyl or naphthyl,
an imidazolyl group optionally reduced and/or substituted by an oxo group,
a group of formula:

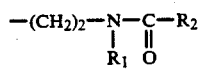

where G represents a linear or branched lower alkyl group, and R₃ and R₄, identical or different, both represent a lower alkyl group or a hydrogen atom or a phenyl or lower phenylalkyl group, or R₃ and R₄ form, with the nitrogen atom to which they are attached, a mono- or bicyclic heterocyclic system which may or may not be aromatic, with each ring having five or six apexes optionally including another heteroatom and being optionally substituted by one or more lower alkyl, or oxo, aryl or lower arylalkyl, or substituted aryl or substituted lower arylalkyl groups, it being understood that the term substituted qualifying the aryl and arylalkyl, and heteroaryl, groups in the definition of R₂, R₃ and R₄ means that these groups are substituted by one or more radicals chosen from among lower alkyl, lower alkoxy, trifluoromethyl or a halogen atom, or R₁ forms with R₂ and the N-CO group a heterocyclic system of formula:

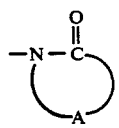

with A being a linear or branched alkyl radial comprising 2 to 8 carbon atoms, their isomers, epimers and diastereoisomers as well as, if the case arises, their addition salts with a pharmaceutically acceptable acid, it being understood that lower alkyl and lower alkoxy mean groups comprising 1 to 6 carbon atoms and that cycloalkyl means groups comprising 3 to 8 carbon atoms.

Among the pharmaceutically acceptable acids which can, if the case arises, be added to compounds of formula (I) to obtain a salt there may be mentioned, without implied limitation, hydrochloric, sulfuric, tartaric, maleic, fumaric, oxalic, methanesulfonic and camphoric acids, etc.

The subject of the present invention is also a process for preparing compounds of formula (I), which comprises using as starting material a compound of formula (II):

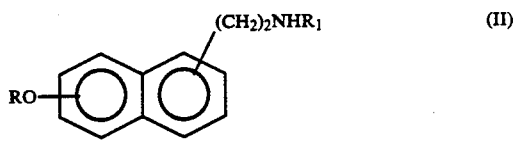

(II)

in which R and R₁ have the same meaning as in formula (I), which is treated
either with a compound of formula (III):

(III)

in which E means a starting group chosen from among hydroxyl, lower alkoxy or a halogen, and G, $R_3$ and R have the same meaning as in formula (I), optionally in the presence of an alkaline agent, to lead to a compound of formula (I/A), a particular case of compounds of formula (I):

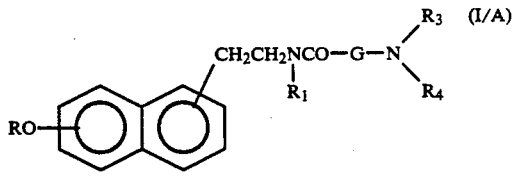

in which R, $R_1$, $R_3$, $R_4$ and G have the same definition as above, $R_2$ here meaning a group

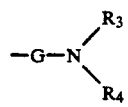

group, which can be purified, if so desired, by conventional techniques such as chromatography and crystallization, and which can be converted into a salt, if so desired, by a pharmaceutically acceptable acid, or with an acyl chloride of formula (IV):

Cl—CO—R'$_2$     (IV)

or with the corresponding acid anhydride, R'$_2$ here meaning
a linear or branched lower alkyl group or a cycloalkyl group optionally substituted by a halogen atom,
an aryl or heteroaryl or lower arylalkyl group, optionally substituted by one or more halogen atoms or groups chosen from among lower alkyl, lower alkoxy or trifluoromethyl,
an imidazolyl group optionally reduced and/or substituted by an oxo group,
to lead to a compound of formula (I/B):

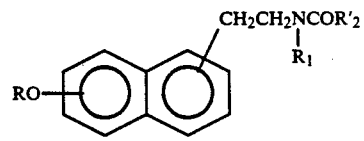

a particular case of compounds of formula (I) in which R, and R'$_2$ have the same definition as above, which can be purified, if necessary, by conventional techniques such as chromatography and/or crystallization, when R'$_2$ represents a linear or branched lower alkyl group substituted by a halogen atom, a compounds of formula (I/B) which, can be subjected, if so desired, to the action of an amine of formula (V):

in which $R_3$ and $R_4$ have the same definition as above, in excess or in the presence of a tertiary amine or of a salt of an alkali metal, to lead to a compound of formula (I/A) as defined above, which, if so desired, is purified by a conventional technique such as chromatography and/or crystallization, and/or converted into a salt by a pharmaceutically acceptable acid, a compound of formula (I/B) which, when R'$_2$ represents a linear or branched alkyl substituent comprising at least two carbon atoms and substituted by a halogen atom, and when simultaneously $R_1$ represents a hydrogen atom, can be subjected, if so desired, to the action of a strong base, and preferably an alcoholate of an alkali metal, to lead to a compound of formula (I/C):

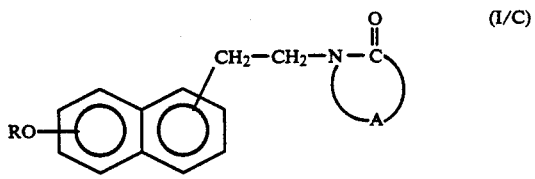

in which R has the same meaning as above and A represents a linear or branched alkyl group comprising 2 to 8 carbon atoms, a particular case of compounds of formula (I) for which $R_1$ and $R_2$ form with NCO a monocyclic system substituted by an oxo group, and optionally substituted by one or more lower alkyl groups, which is purified, if so desired, by a technique chosen from among crystallization and chromatography.

The compounds of formula (I) possess valuable pharmaceutical properties.

Pharmacological study of the compounds s of the invention in fact showed that they have low toxicity, that they are endowed with a very high selective affinity for melatonin receptors, and that they have major effects on the central nervous system, and in particular sedative, anxiolytic, antipsychotic and analgesic properties have been revealed, as well as on the microcirculation which enable us to claim that the products of the invention are useful in the treatment of stress, sleep disorders, anxiety, seasonal depression, insomnia and tiredness due to "jet lag", schizophrenia, panic attacks, melancholy, the regulation of appetite, insomnia, psychotic problems, epilepsy, Parkinson's disease, senile dementia, the various disorders resulting from normal or pathological ageing, migraine, memory loss, Alzheimer's disease, as well as disorders of cerebral circulation.

In another field of activity, it appears that the products of the invention possess properties as inhibitors of ovulation, and as immunomodulators, and that they can therefore be used in the treatment of certain cancers and that, administered externally, they are useful in the treatment of psoriasis, acne, seborrhea, protect the skin and promote the growth of hair. They can also have a veterinary application because of their properties in relation to the coat.

The subject of the present invention is also pharmaceutical compositions containing the products of formula (I) or, if the case arises, of their addition salts with a pharmaceutically acceptable acid, alone or in combination with one or more pharmaceutically acceptable inert non-toxic excipients or vehicles.

Among the pharmaceutical compositions according to the invention there may be mentioned, in particular, those which are suitable for oral, parenteral, nasal, per- or transcutaneous, rectal, perlingual, ocular or respiratory administration, and particularly simple or sugared pills, sublingual tablets, sachets, packets, capsules, glossettes, tablets, suppositories, creams, ointments, dermal gels, phials for oral and injectable use, and the like.

Dosage varies according to the age and weight of the patient, the route of administration, the indications for treatment or the treatments with which it may be associated, and ranges between 0.1 mg and 1 gram in 24 hours.

The following examples illustrate the invention, without limiting it in any way.

The products described in the "preparations" are not part of the invention. Their description, however, facilitates the realization of the compounds of the invention.

PREPARATION 1

2-(7-Methoxynaphth-1-yl)ethylamine

Stage A: Ethyl (7-methoxy-1,2,3,4-tetrahydro-1-naphthylidene)acetate 50 of 7-methoxy-1-tetralone, 40 g of ethyl 50 g bromoacetate and 150 ml of benzene are mixed via a dropping funnel. Activated zinc filings (18.6 g) are added to the mixture for the Reformatsky reaction, followed by an iodine crystal. The mixture is heated to 60° C. and then refluxed for 45 minutes.

The mixture is hydrolyzed under ice in the presence of hydrochloric acid, extracted with benzene, dried and boiled in the presence of $P_2O_5$. It is then filtered and dried.

The residue is used as such in the following step.
Yield: 80%

Stage B: Ethyl (7-methoxynaphth-1-yl)acetate 7.35 g of sulfur are mixed with 50 g of ethyl (7-methoxy-1,2,3,4-tetrahydro-1-naphthylidene)acetate and the mixture is heated at 215° C. for 10 hours. It is then cooled and 300 ml of ethyl acetate are added; the mixture is agitated for 30 minutes, filtered and then dried.

The residue obtained is used as such in the saponification step.
Yield: 70%

Stage C: (7-Methoxynaphth-1-yl)acetic acid

A mixture of the ethyl (7-methoxynaphth-1-yl) acetate obtained above in 250 ml of a 20% ethanolic sodium hydroxide solution is heated under reflux for 3 hours.

The mixture is dried, and the residue is washed in ether and precipitated by a current of hydrogen chloride gas.

Melting point: 155°–156° C.
Yield: 68%

Stage D: (7-Methoxynaphth-1-yl)acetyl chloride

The (7-methoxynaphth-1-yl)acetic acid obtained above is dissolved by heating in 300 ml of chloroform. The mixture is heated under reflux, and then thionyl chloride is added dropwise. The mixture is refluxed for two hours and evaporated to dryness. An oil is obtained which crystallizes on cooling. The residue obtained is used as such in the following stage.

Stage E: (7-Methoxynaphth-1-yl)acetamide

The (7-methoxynaphth-1-yl)acetyl chloride obtained above is dissolved in 200 ml of anhydrous ether. After cooling the solution in an ice/salt bath, 200 ml of concentrated aqueous ammonia solution are added with agitation. The mixture is agitated for 30 minutes and the precipitate formed is spun down and recrystallized in ethanol.
Yield: 95%
Melting point: 201°–202° C.

Stage F: (7-Methoxynaphth-1-yl)acetonitrile

The (7-methoxynaphth-1-yl)acetamide obtained in Stage E is suspended in 80 ml of anhydrous THF, and triethylamine is added. The solution is cooled in an ice bath, and then trifluoroacetic anhydride is added dropwise with magnetic agitation. Agitation is continued for one hour at room temperature. Then the mixture is dried and the residue taken up in water. The precipitate which forms is spun down, dried and recrystallized in isopropyl ether.
Yield: 83%
Melting point: 82°–84° C.
Spectral characteristics: Infrared: 2240 cm$^{-1}$ CN Stage G: 2-(7-Methoxynaphth-1-yl)ethylamine A solution of (7-methoxynaphth-1-yl)acetonitrile in ethanol saturated with ammonia is placed in an autoclave. Raney nickel and hydrogen at 300 atmospheres are added. The mixture is agitated at 60° C overnight and then filtered; the filtrate is evaporated under vacuum and the oil thus obtained is used as starting material.

PREPARATION 2

(7-Methoxynaphth-1-yl)ethyl]n-methylamine

The product of the title is obtained by following the same procedure as in Preparation 1, but replacing ammonia by methylamine at Stage E.

PREPARATION 3

6-Methoxynaphth-1-yl)ethylamine

The product title is obtained by following the same procedure as in Preparation 1, but replacing 7-methoxy-1-tetralone by 6-methoxy-1-tetralone at Stage A.

PREPARATION 4

2-(5-Methoxynaphth-1-yl)ethylamine

The product of the title is obtained by following the same procedure as in Preparation 1, but replacing 7-methoxy1-tetralone by 5-methoxy-1-tetralone at Stage A.

PREPARATION 5

2-(7-Methoxynaphth-2-yl)ethylamine

The product of the title is obtained by following the same procedure as in Preparation 1, but replacing 7-methoxy-1-tetralone by 7-methoxy-2-tetralone at Stage A.

PREPARATION 6

2-(6-Methoxynaphth-2-yl)ethylamine

The product of the title is obtained by following the same procedure as in Preparation 1, but replacing 7-methoxy-1-tetralone by 6-methoxy-2-tetralone at Stage A.

EXAMPLE 1

N-[2-(7-methoxynaphth-1-yl)ethyl]acetamide 0.01 ml of 2-(7-methoxynaphth-1-yl)ethylamine is dissolved in 6 ml of pyridine. The mixture is cooled in an ice bath with agitation, and 0.012 mol of acetyl chloride is added dropwise.

The agitation is maintained for 30 minutes, and then the reaction medium is poured onto ice. The precipitate formed is spun down, washed, dried and recrystallized in isopropyl ether.
Yield: 92%
Melting point: 109°–110° C.
Spectral characteristics: Infrared: 3240 cm$^{-1}$ vNH 1640 cm$^{-1}$ vCO 1H Nuclear maonetic resonance, solvent CDCl$_3$ δ: 1.93 ppm, singlet, 3H, COCH₃
δ: 3.96 ppm, singlet, 3H, OCH₃

EXAMPLE 2

N-[2-(7-methoxynaphth-1-yl)ethyl]phenylacetamide 0.01 mol of 2-(7-methoxynaphth-1-yl)ethylamine hydrochloride (obtained by dissolving 2-(7-methoxynaphth-1-yl)ethylamine in ether and bubbling through a current of hydrogen chloride gas, then spinning down the precipitate formed) is dissolved in 60 ml of a water/chloroform mixture. 0.01 mol of potassium carbonate is added under magnetic agitation.

The mixture is cooled and 0.012 mol of phenylacetyl chloride is added dropwise. The agitation is maintained for 30 minutes at room temperature, the chloroform phase is dried and the residue is recrystallized in isopropyl ether.

Yield: 92%
Melting point: 101°-102° C.
Spectral characteristics: Infrared: 3220 cm⁻¹ νNH 1640 cm⁻¹ νCO 1H Nuclear magnetic resonance, Solvent CDCL₃
δ: 3.50 ppm, clump, 2H, CH₂-N
δ: 3.93 ppm, singlet, 1H, OCH₃

EXAMPLE 3

N-[2-(7-methoxynapth-1-yl)ethyl]-isobutyramide

The product of the title is obtained by following the same procedure as in Example 1, but replacing acetyl chloride by isobutyryl chloride.

Yield: 91%
Melting point: 77°-78° C.
Spectral characteristics: Infrared: 3240 cm⁻¹ νNH 1640 cm⁻¹ νCO 1620 cm⁻¹ νCC 1H Nuclear maonetic resonance, Solvent CDCl₃
δ: 1.11 ppm, doublet, 6H, 2CH₃ (isopropyl)
δ: 2.29 ppm, multiplet, 1H, CH (COCH)
δ: 3.98 ppm, singlet, 3H, OCH₃

EXAMPLE 4

N-[2-(7-methoxynaphth-1-yl)ethyl]propionamide

The product of the title is obtained by following the same procedure as in Example 1, but replacing acetyl chloride by propionyl chloride.

Melting point: 104°-104.5° C.

EXAMPLE 5

N-[2-(7-methoxynaphth-1yl)ethyl]pentanamide

The product of the title is obtained by following the same procedure as in Example 1, but replacing acetyl chloride by pentanoyl chloride.

Crystallising solvent: cylcohexane
Melting point: 90° C.

EXAMPLE 6

N-[2-(7-methoxynaphth-1-yl)ethyl]-(2-oxopyrrolidin-1-yl)acetamide or
1-{2-[(2-Oxopyrrolidin-1-yl)acetamido]ethyl)-7-Methoxynaphthalene

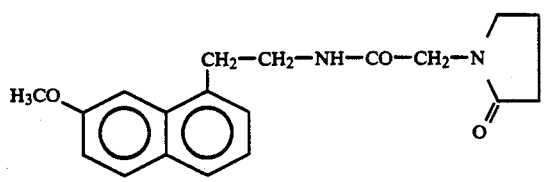

A mixture of 0.02 mol of 2-(7-methoxynaphth-1-yl)ethylamine and 0.022 mol of methyl (-2-oxo-pyrrolidin-1yl)acetate is heated under magnetic agitation at a temperature of 80° C. for 3 hours.

The reaction medium is taken up in slightly acid water, and the precipitate formed is spun down and recrystallized in di-n-butyl ether.

Yield: 55%
Melting point: 125°-126° C.
Spectral characteristics:
Infrared: 3310 cm⁻¹ νNH
3060-2820 cm⁻¹ νCH(CH₂CH₂)
1690 cm⁻¹ νCO (CON)
1630-1600 cm⁻¹ νCC (aromatic)
1030 cm⁻¹ νOCH₃

¹H Nuclear magnetic resonance, Solvent CDCl₃
δ: 3.88 ppm, singlet, 2H, NHCOCH₂
δ: 4 00 ppm, singlet, 3H, OCH₃

EXAMPLE 7

N-[2-(7-methoxynaphth-1-yl)ethyl]-4chlorobutyramide 0.02 mol of 2-(7-methoxynaphth-1-yl)ethylamine hydrochloride is dissolved in a water/chloroform mixture. Potassium carbonate is added and the mixture is agitated for 15 minutes in an ice bath. 0.022 mol of 4-chlorobutyryl chloride is then added dropwise. The agitation is maintained for half an hour at room temperature; then the chloroform phase is dried, and the residue is recrystallized in a toluene/cyclohexane mixture (1:1).

Yield: 93%
Melting point: 97°-98° C.
Spectral characteristics: Infrared:
3320 cm⁻¹ νNH
1635 cm⁻¹ νCO

EXAMPLE 8

N-[2-(7-methoxynaphth-1-yl)ethyl]pyrrolidin-2-one 0.01 mol of sodium is dissolved in 50 ml of ethanol and the N-[2-(7-methoxynaphth-1-yl)ethyl]chloro-4-butyramide obtained in Example 7 is added under magnetic agitation. The agitation is maintained for 20 minutes, and then the mixture is dried and the residue is solubilized in 40 ml of anhydrous dimethylformamide. The solution is heated at boiling point for 7 hours, then evaporated under vacuum and the residue is taken up in ether, then filtered and dried. The residue is recrystallized in petroleum ether.

Yield: 35%
Melting point: 60°-61° C.
Spectral characteristics: Infrared:

3060–2820 cm$^{-1}$ vCH
1670 cm$^{-1}$ vCO

EXAMPLE 9

N-[2-(7-methoxynaphth-1-yl)ethyl)-2-bromoacetamide

The same procedure as in Example 7, replacing 4-chlorobutyryl chloride by bromoacetyl chloride.
Melting point: 100°–101° C.
Yield: 93%
Spectral characteristics: Infrared:
3260 cm$^{-1}$ vNH
1635 cm$^{-1}$ vCO $^1$H Nuclear magnetic resonance, Solvent CDCl$_3$
δ: 2.83 ppm, singlet, 2H, (CH$_2$Br)
δ: 3.98 ppm, singlet, 3H, (OCH$_3$)

EXAMPLE 10

N-[2-(7-methoxynaphth-1-yl)ethyl]-2-morpholinoacetamide 0.01 mol of morpholine is dissolved under magnetic agitation in 50 ml of acetone, and 0.012 mol of triethylamine and 0.01 mol of N-[2-(7-methoxynaphth-1-yl)ethyl]-2-bromoacetamide are added. The mixture is refluxed for 1 hour under magnetic agitation. The precipitate formed is spun down and the filtrate is evaporated. The residue is taken up in alkaline water, and the precipitate is spun down, washed, dried and recrystallized in a toluene/cyclohexane mixture.

Spectral characteristics: Infrared: 1645 cm$^{-1}$ vCO
$^1$H Nuclear maonetic resonance, Solvent CDCl$_3$
δ: 3.98 ppm, singlet, 3H, OCH$_3$
δ: 2.92 ppm, singlet, 2H, (CO—CH$_2$)
Melting point: 114°–115° C.
Yield: 93%

EXAMPLE 11

N-[2-(7-Methoxynaphth-1-yl)ethyl]-2-{4-[(2,3,4-trimethoxyphenyl)methyl]piperazin-1-yl}acetamide hydrochloride The product of the title is obtained by proceeding as in the previous example, but replacing morpholine by 1-[(2,3,4-trimethoxyphenyl)methyl]piperazine. The hydrochloride is obtained by dissolving the product in acetone, bubbling a current of hydrogen chloride gas, evaporation and recrystallization in absolute alcohol.
Spectral characteristics: Infrared: 1670 cm$^{-1}$ vCO
$^1$H Nuclear magnetic resonance, Solvent CDCl$_3$
δ: 3.99 ppm, singlet, 3H, OCH$_3$:
Melting point: 207°–208° C.
Yield: 90%

EXAMPLE 12

N-[2-(7-methoxynaphth-1-yl)ethyl]-N-methylacetamide

The product of the title is obtained by replacing 2-(7-methoxynaphth-1-yl)ethylamine in Example 1 by N-[2-(7-methoxynaphth-1-yl)ethyl]-N-methylamine.
Spectral characteristics: Infrared: 1640 cm$^{-1}$ vCO
$^1$H Nuclear maonetic resonance, Solvent CDCl$_3$
δ: 3.98 ppm, singlet, 3H, OCH$_3$

EXAMPLE 13

N-[2-(7-methoxynaphth-1-yl)ethyl]benzamide

The product of the title is obtained by replacing phenacetyl chloride in Example 2 by benzoyl chloride.

Spectral characteristics: Infrared: 1640 cm$^{-1}$ vCO
$^1$H Nuclear magnetic resonance, Solvent CDCl$_3$
δ: 3.98 ppm, singlet, 3H, OCH$_3$
Melting point: 128°–130° C.
Yield: 94%

EXAMPLE 14

N-[2-(7-methoxynaphth-1-yl)ethyl]paratoluoyl carboxamide

The product of the title is obtained by replacing phenylacetyl chloride in Example 2 by paratoluoyl chloride.
Spectral characteristics: Infrared: 1635 cm$^{-1}$ vCO
$^1$H Nuclear maonetic resonance, Solvent CDCl$_3$
δ: 3.95 ppm, singlet, 3H, OCH$_3$

EXAMPLE 15

N-[2-(7-methoxynaphth-1-yl)ethyl]-4-fluorobenzamide

The product of the title is obtained by replacing phenylacetyl chloride in Example 2 by parafluorobenzoyl chloride.
Spectral characteristics: Infrared: 1635 cm$^{-1}$ vCO
$^1$H Nuclear magnetic resonance, Solvent CDCl$_3$
δ: 3.95 ppm, singlet, 3H, OCH$_3$

EXAMPLE 16

N-[2-(7-Methoxynaphth-1-yl)ethyl]-3-trifluoromethyl-benzamide

The product of the title is obtained by replacing phenylacetyl chloride in Example 2 by 3-trifluoromethylbenzoyl chloride.
Spectral characteristics: Infrared: 1635 cm$^{-1}$ vCO
$^1$H Nuclear magnetic resonance, Solvent CDCl$_3$:
δ: 3.95 ppm, singlet, 3H, OCH$_3$

EXAMPLE 17

N-[2-(7-Methoxynaphth-1-YL)ETHYL]-3,5-dichlorobenzamide

The product of the title is obtained by replacing phenacetyl chloride in Example 2 by 3,5-dichlorobenzoyl chloride.
Yield: 93%
Melting point: 138° C.

EXAMPLE 18

N-[2-(7-methoxynaphth-1-yl)ethyl]-isonicotinamide

The product of the title is obtained by replacing phenacetyl chloride in Example 2 by isonicotinoyl chloride.
Spectral characteristics: Infrared: 1635 cm$^{-1}$ vCO
$^1$H Nuclear magnetic resonance, Solvent CDCl$_3$: δ: 3.95 ppm, singlet, 3H, OCH$_3$

EXAMPLE 19

N-[2-(7-methoxynaphth-1-yl)ethyl]-2-thiophenecarboxamide

The product of the title is obtained by replacing phenylacetyl chloride in Example 2 by 2-thiophene carbonyl chloride.
Spectral characteristics: Infrared: 1635 cm$^{-1}$ vCO
$^1$H Nuclear magnetic resonance, Solvent CDCl$_3$:
δ: 3.95 ppm, singlet, 3H, OCH$_3$

EXAMPLE 20

N-[2-(7-Methoxynaphth-1-yl)ethyl]-2-quinoxalinecarboxamide

The product of the title is obtained by replacing phenylacetyl chloride in Example 2 by 2-quinoxaloyl chloride.

Spectral characteristics: Infrared: 1635 cm$^{-1}$ vCO
$^1$H Nuclear magnetic resonance, Solvent CDCl$_3$:
δ: 3.95 ppm, singlet, 3H, OCH$_3$

EXAMPLE 21

N-[2-(7-methoxynaphth-1-yl)ethyl]indole-carboxamide

The product of the title is obtained by replacing phenacetyl chloride in Example 2 by 2-indolyl chloride.

Melting point: 198°-199° C.
Spectral characteristics:
Infrared:
3400 cm$^{-1}$ vNH (indole)
3300 cm$^{-1}$ vNH
1640 cm$^{-1}$ vCO
$^1$H Nuclear maonetic resonance, Solvent CDCl$_3$
δ: 3.98 ppm, singlet., 3H, OCH$_3$

EXAMPLE 22

N-[2-(7-methoxynaphth-1-yl)ethyl]-2-benzylaminoacetamide

The product of the title is obtained by following the same procedure as in Example 10 and by replacing morpholine by benzylamine.

Spectral characteristics: Infrared: 1635 cm$^{-1}$ vCO
$^1$H Nuclear magnetic resonance. Solvent CDCl$_3$:
δ: 3 95 ppm, singlet, 3H, OCH$_3$

EXAMPLE 23

N-[2-(7-Methoxynaphth-1-yl)ethyl]-2-(N',N'-diethyl)aminoacetamide

The product of the title is obtained by following the same procedure as in Example 10, but replacing morpholine by N,N-diethylamine.

Spectral characteristics: Infrared: 1635 cm$^{-1}$ vCO
$^1$H Nuclear magnetic resonance, Solvent CDCl$_3$:
δ: 3.95 ppm, singlet, 3H, OCH$_3$

EXAMPLE 24

N-[2-(7-methoxynaphth-1yl)ethyl-2-aminoacetamide hydrochloride 0.012 mol of hexamethylenetetramine is dissolved under magnetic agitation in 15 ml of chloroform, and 0.01 mol of N-[2-(7-methoxynaphth-1-yl)ethyl]-2-bromoacetamide obtained in Example 9 dissolved in 20 ml of chloroform are introduced. The mixture is refluxed for 100 hours, spun down and dried. The precipitate is introduced into a ground glass flask and 150 ml of alcohol and 30 ml of concentrated hydrochloric acid are added. The mixture is refluxed for two hours, and then the solvent is evaporated and the residue is recrystallized in alcohol at 90° C.

Spectral characteristics: Infrared: 1635 cm$^{-1}$ vCO
$^1$H Nuclear magnetic resonance, Solvent CDCl$_3$:
δ: 3.95 ppm, singlet, 3H, OCH$_3$

EXAMPLE 25

N-[2-(7-Methoxynaphth-1-yl)Ethyl]2-[4-(4-Fluorophenyl)piperazin-1-yl]Acetamide

The product of the title is obtained by following the same procedure as in Example 10, but replacing morpholine by 1-(4-fluorophenyl)piperazine.

EXAMPLE 26

N-[2-(7-Methoxynaphth-1-yl)Ethyl]-2-[4-(3-Trifluoromethylphenyl)piperazin-1-l]acetamide The product of the title is obtained by following the same procedure as in Example 10, but replacing morpholine by 1-(3-trifluoromethylphenyl)piperazine.

EXAMPLE 27

N-[2-(7-Methoxynaphth-1-yl)Ethyl]-Butyramide

The product of the title is obtained by following the same procedure as in Example 1, but replacing acetyl chloride by butyryl chloride.

Melting point 99° C.

EXAMPLE 28

N-[2-(7-Methoxynaphth-1-yl)Ethyl]-4-Imidazolylacetamide 0.01 mol of 2-(7-methoxynaphth-1-yl)ethylamine hydrochloride is dissolved in 60 ml of a chloroform/water mixture, and 0.025 mol of potassium carbonate is added under magnetic agitation. The mixture is cooled, and 0.012 mol of 4-imidazoleacetyl chloride hydrochloride is added dropwise. The agitation is maintained for 30 minutes at room temperature and the chloroform phase is evaporated to dryness. The residue is then recrystallized.

Yield: 67%

Spectral characteristics: Infrared: 1640 cm$^{-1}$ vCO $^1$H Nuclear maonetic resonance, Solvent CDCl$_3$ δ=3.91 ppm, singlet, 1H, OCH$_3$

EXAMPLE 29

N-[2-(7-Methoxynaphth-1-yl)Ethyl]-2-Imidazolinone-4-Carboxamide

The product of the title is obtained by following the same procedure as in Example 1, but replacing acetyl chloride by 2-imidazolinone-4-carboxyl chloride.

Yield: 55%
Spectral characteristics:
$^1$H Nuclear magnetic resonance, Solvent CDCl$_3$
δ=3.89 ppm, singlet, 1H, OCH$_3$

EXAMPLE 30

N-[2-(7-Methoxynaphth-1-yl)Ethyl]Cyclohexanecarboxamide (R$_2$=cyclohexyl)

The product of the title is obtained by following the same procedure as in Example 1, but replacing acetyl chloride by cyclohexanecarboxyl chloride.

Recrystallizing solvent: cyclohexane
Melting point: 105°-106° C.

EXAMPLE 31

N-[2-(7-Methoxynaphth-1-yl)Ethyl]Cyclopropanecarboxamide ($R_2$=cyclopropyl)

The product of the title is obtained by following the same procedure as in Example 1, but replacing acetyl chloride with cyclopropylcarboxyl chloride.
Crystallizing solvent: cyclohexane
5 Melting point: 91-92° C.

EXAMPLE 32

N-[2-(7-Methoxynaphth-1-yl)Ethyl]Iodoacetamide

The product of the title is obtained by treating the N-[2-(7-methoxynaphth-1-yl)ethyl]-2-bromoacetamide obtained in Example 9 with potassium iodide.
Recrystallizing solvent: ethanol Melting point: 110-112° C.

EXAMPLE 33

N-[2-(7-Methoxynaphth-1-yl)Ethyl]Formamide 0.01 mol of 2-(7-methoxynaphth-1-yl)ethylamine and 0.02 mol of formic acid are placed in a porcelain crucible, and heated at 120° C. until a dry residue is obtained. This is recrystallized.
Melting point: 93° C.
Spectral characteristics:
Nuclear magnetic resonance:
δ: 4.05 ppm, singlet, 3H, $OCH_3$

EXAMPLE 34

N-[2-(7-Methoxynaphth-1-yl)Ethyl]Cyclobutanecarboxamide

The product of the title is obtained by following the same procedure as in Example 1, but replacing acetyl chloride by cyclobutanecarboxyl chloride.

EXAMPLE 35

N-[2-(7-Methoxynaphth-1-yl)Ethyl]Cyclopentanecarboxamide

The product of the title is obtained by following the same procedure as in Example 1, but replacing acetyl chloride by cyclopentanecarboxyl chloride.
Proceeding according to the preceding examples, one also obtains:
N-[2-(7-METHOXYNAPHTH-1-YL)ETHYL]-4-BROMOBUTYRAMIDE
N-[2-(7-METHOXYNAPHTH-1-YL)ETHYL]-5-BROMOPENTANAMIDE
N-[2-(7-METHOXYNAPHTH-1-YL)ETHYL]-3-BROMOPROPIONAMIDE
N-[2-(7-METHOXYNAPHTH-1-YL)ETHYL]-3-MORPHOLINOPROPIONAMIDE
N-[2-(7-METHOXYNAPHTH-1-YL)ETHYL]-3-MORPHOLINOBUTYRAMIDE
N-[2-(7-METHOXYNAPHTH-1-YL)ETHYL]-4-{4-[(2,3,4-TRIMETHOXY-PHENYL)METHYL]-PIPERAZIN-1-YL}BUTYRAMIDE
N-[2-(7-METHOXYNAPHTH-1-YL)ETHYL]-3-{4-[(2,3,4TRIMETHOXY-PHENYL)METHYL]-PIPERAZIN-1-YL}PROPIONAMIDE
N-[2-(7-METHOXYNAPHTH-1-YL)ETHYL]-PIPERIDIN-2-ONE N-[2-(7-METHOXYNAPHTH-1-YL)ETHYL]-2-BROMOPROPIONAMIDE
N-[2-(7-METHOXYNAPHTH-1-YL)ETHYL]-2-{4-[(2,3,4TRIMETHOXY-PHENYL)METHYL]PIPERAZIN-1-YL}PROPIONAMIDE By replacing 2-(7-methoxynaphth-1-yl)ethylamine in the preceding examples by 2-(6-methoxynaphth-1-yl)ethylamine ethylamine or by 2-(5-methoxynaphth-1-yl)ethylamine, the products of the preceding examples methoxylated at position 6 or 5 on the naphthalene respectively are obtained in place of the derivatives methoxylated at position 7.

By replacing 2-(7-methoxynaphth-1-yl)ethylamine in the preceding examples by 2-(7-methoxynaphth-2yl)ethylamine, one obtains:
N-[2-(7-METHOXYNAPHTH-2-YL)ETHYL]ACETAMIDE
N-[2-(7-METHOXYNAPHTH-2-YL)ETHYL]-PHENYLACETAMIDE
N-[2-(7-METHOXYNAPHTH-2-YL)ETHYL]ISOBUTYRAMIDE
N-[2-(7-METHOXYNAPHTH-2-YL)ETHYL]PROPIONAMIDE
N-[2-(7-METHOXYNAPHTH-2-YL)ETHYL]PENTANAMIDE
N-[2-(7-METHOXYNAPHTH-2-YL)ETHYL]-(2-OXOPYRROLIDIN-1-YL)ACETAMIDE
N-[2-(7-METHOXYNAPHTH-2YL)ETHYL]-4-CHLOROBUTYRAMIDE
N-[2-(7-METHOXYNAPHTH-2-YL)ETHYL]PYRROLIDIN-2-ONE
N-[2-(7-METHOXYNAPHTH-2-YL)ETHYL]-2-BROMOACETAMIDE
N-[2-(7-METHOXYNAPHTH-2-YL)ETHYL]-2-MORPHOLINOACETAMIDE
N-[2-(7-METHOXYNAPHTH-2-YL)ETHYL]-2-{4-[(2,3,4-TRIMETHOXY-PHENYL)METHYL]PIPERAZIN-1-YL}ACETAMIDE HYDROCHLORIDE
N-[2-(7-METHOXYNAPHTH-2-YL)ETHYL]-N-METHYLACETAMIDE
N-[2-(7-METHOXYNAPHTH-2-YL)ETHYL]BENZAMIDE
N-[2-(7-METHOXYNAPHTH-2-YL)ETHYL]-PARATOLUOYLCARBOXAMIDE
N-[2-(7-METHOXYNAPHTH-2-YL)ETHYL]-4-FLUOROBENZAMIDE
N-[2-(7-METHOXYNAPHTH-2-YL)ETHYL]-3-TRIFLUOROMETHYLBENZAMIDE
N-[2-(7-METHOXYNAPHTH-2-YL)ETHYL]-3,5-DICHLOROBENZAMIDE
N-[2-(7-METHOXYNAPHTH-2-YL)ETHYL]ISONICOTINAMIDE
N-[2-(7-METHOXYNAPHTH-2-YL)ETHYL]-2-THIOPHENECARBOXAMIDE
N-[2-(7-METHOXYNAPHTH-2-YL)ETHYL]-2-QUINOXALINECARBOXAMIDE
N-[2-(7-METHOXYNAPHTH-2-YL)ETHYL]INDOL-2-YLCARBOXAMIDE
N-[2-(7-METHOXYNAPHTH-2-YL)ETHYL]-2-BENZYLAMINOACETAMIDE
N-[2-(7-METHOXYNAPHTH-2-YL)ETHYL]-2-(N',N'-DIETHYL)AMINOACETAMIDE
N-[2-(7-METHOXYNAPHTH-2-YL)ETHYL]-2-AMINOACETAMIDE
N-[2-(7-METHOXYNAPHTH-2-YL)ETHYL]-2-[4-(4-FLUOROPHENYL)PIPERAZIN-1-YL]ACETAMIDE N-[2-(7-METHOXYNAPHTH-2-YL)ETHYL]-2-[4-(3-TRIFLUOROMETHYLPHENYL)PIPERAZIN-1-YL]ACETAMIDE

N-[2-(7-METHOXYNAPHTH-2-YL)ETHYL]-BUTYRAMIDE

N-[2-(7-METHOXYNAPHTH-2-YL)ETHYL]-4-IMIDAZOLYLACETAMIDE

N-[2-(7-METHOXYNAPHTH-2-YL)ETHYL]-2-IMIDAZOLINONE-4-CARBOXAMIDE

N-[2-(7-METHOXYNAPHTH-2-YL)ETHYL]CYCLOHEXANECARBOXAMIDE

N-[2-(7-METHOXYNAPHTH-2-YL)ETHYL]CYCLOPROPANECARBOXAMIDE

N-[2-(7-METHOXYNAPHTH-2-YL)ETHYL]IODOACETAMIDE

N-[2-(7-METHOXYNAPHTH-2-YL)ETHYL]FORMAMIDE

N-[2-(7-METHOXYNAPHTH-2-YL)ETHYL]CYCLOBUTANECARBOXAMIDE

N-[2-(7-METHOXYNAPHTH-2-YL}ETHYL]CYCLOPENTANECARBOXAMIDE

If in these syntheses 2-(7-methoxynaphth-2-yl)ethylamine is replaced by 2-(6-methoxynaphth-2-yl)ethylamine, isomers of the preceding products are obtained with the methoxy group at position 6.

PHARMACOLOGICAL STUDY OF THE COMPOUNDS OF THE INVENTION

EXAMPLE A

STUDY OF ACUTE TOXICITY

Acute toxicity was estimated after oral administration to groups of 8 mice (26±2 grams). The animals were observed at regular intervals during the course of the first day, and daily for 2 weeks following treatment. The LD50 bringing about the death of 50% of the animals was evaluated.

The LD50 of the products tested is greater than 1000 mg.kg$^{-1}$ for most of the compounds studied, which indicates that the compounds of the invention have low toxicity.

EXAMPLE B

MEASUREMENT OF ACTIVITY

The animals were placed in plexiglass boxes equipped with photoelectric cells placed in a darkened environment. Six animals were tested at the same time, and the number of interruptions of the photoelectric beams by each animal was recorded by computer during one hour.

The compounds tested were administered intraperitoneally immediately before placing the animals in the cages.

The compounds of the invention decreased the activity of the animals.

EXAMPLE C

THE FOUR PLATE TEST

The products of the invention were administered intra-esophageally to groups of 10 mice. One group received acacia syrup. 30 minutes after administering the products being tested, the animals were placed in cages, the floors of which were made up of 4 metal plates. Each time an animal passes from one plate to another it receives a mild electric shock (0.35 mA). The number of times the mice passed from one plate to another were recorded for one minute. After administration, the compounds of the invention significantly increased the number of times that mice passed from one plate to another, showing the anxiolytic activity of these derivatives of the invention.

EXAMPLE D

THE ACTIVITY OF THE PRODUCTS OF THE INVENTION ON THE ISCHEMIC MICROCIRCULATION

The experimental study was performed on the cremaster muscles of male Sprague Dawley rats after ligation of the common iliac artery.

The muscles were placed in a transparent chamber perfused with a bicarbonate buffer solution equilibrated with a gaseous mixture of $CO_2/N_2$ (5/95%). The speed of the erythrocytes and the diameter of the first or second order arterioles irrigating the cremaster were measured, and the arteriolar blood flow was calculated. Identical information was obtained for four different types of vein.

The same type of measurement was made simultaneously:

on the normal perfused cremaster, on ligatured cremaster, i.e. the ischemic cremaster, 2, 7, 14 and 21 days after ligature.

Two groups of animals were studied:

an untreated control group, a group treated per os with a product of the invention at the rate of 0.1 mg.kg$^{-1}$ per day.

No difference was noted in the treated animals in comparison with the controls in the velocity of the erythrocytes, nor in the diameter of the blood vessels in the normally irrigated cremaster muscles.

On the other hand, in the ischemic cremaster muscle the mean diameter of the arterioles was better in the treated animals than in the controls. The velocity of the erythrocytes was normalized by treatment for 21 days.

In fact, in the treated animals the velocity of the erythrocytes and the blood flow measured 7 days after ligature did not differ significantly from the values obtained in the non-ischemic cremaster. These results were obtained without modifying arterial blood pressure.

These results indicate that long-term treatment with a compound of the invention improves the microcirculation and irrigation with blood of ischemic areas.

EXAMPLE E

STIMULATION OF THE IMMUNE RESPONSE

Groups of 6 mice were administered sheep erythrocytes. These groups of mice were then treated subcutaneously with the compounds of the invention for 6 days, and a control group was treated with a placebo. The mice were then left alone for 4 weeks and then received a repeat injection of sheep erythrocytes without receiving any more administrations of a product of the invention. The immune response was evaluated 3 days after the repeat injection. It was significantly enhanced in the groups treated with the compounds of the invention.

EXAMPLE F

INHIBITION OF OVULATION

Adult female rats with regular 4-day cycles were used.

Vaginal swabs were taken daily and the rats were selected after they showed at least two consecutive cycles of four days.

Each cycle is made up of two days of diestrus, one day of proestrus and one day of estrus.

In the afternoon of the day of proestrus, luteinizing hormone is released into the blood by the hypophysis. This hormone induces ovulation, which is indicated by the presence of ova in the oviduct on the day of estrus.

The compounds of the invention were administered orally at midday on the day of estrus. The treated and control rats were sacrificed on the day of estrus and the oviducts were examined. A significant percentage decrease in the number of ova was noted in the oviducts of treated rats.

EXAMPLE G

DEMONSTRATION OF ANALGESIC ACTIVITY

The effect on pain was studied in mice (23-25 g) according to a protocol derived from the technique described by SIEGMUND (SIEGMUND E. A., CADMUS R. A. & GOLU: J. Pharm. Exp. Ther. 119, 1874 (1954)}. Mice divided by randomization into groups of 12 animals received the treatment orally (excipient in the case of controls) 1 hour before intraperitoneal injection of an aqueous alcoholic solution of phenyl-p-benzoquinone (Sigma) at 0.02%. Stretching movements were counted between the 5th and 10th minute after the injection.

It appeared that certain compounds of the invention possess analgesic activity.

EXAMPLE H

POTENTIALIZATION OF BARBITURATE-INDUCED SLEEP

Mice (22-25 g) were injected intraperitoneally with pentobarbital at 50 mg.kg . The time of appearance and the duration of sleep were measured. It was recognized that the animals were asleep when they lost the righting reflex. The compounds to be tested were administered intraperitoneally 30 minutes before the barbiturate injection. Certain products of the invention increased the duration of sleep induced by pentobarbital.

EXAMPLE I

TEST OF BINDING TO MELATONIN RECEPTORS

Binding of compounds of the invention to melatonin receptors was carried out according to conventional techniques. It appears that the compounds of the invention bind very specifically to melatonin receptors with an affinity greater than for melatonin itself. The most beneficial have a $K_d$ of $5.5 \times 10^{-13}$, while melatonin itself possesses a $K_d$ of $6.3 \times 10^{11}$, which means that certain products of the invention have a selective affinity for melatonin receptors which is 100 times greater than for melatonin itself.

EXAMPLE J

STUDY OF BLOOD GLUCOSE-LOWERING ACTIVITY

Male KK mice were placed in cages at the age of eight weeks. They were used for the experiment when their weight was greater than 40 grams at the age of 4-5 months.

The compound of the invention was suspended in acacia syrup. Each compound tested was administered orally 18 hours before blood sampling.

Blood was collected by sampling from the caudal vein in a hematocrit tube, and then centrifuged. The plasma was collected and the blood glucose concentration was determined.

It appears that certain compounds of the invention significantly decrease blood glucose.

EXAMPLE K

PHARMACEUTICAL COMPOSITION: TABLETS

Tablets containing 50 mg of N-[2-(7-methoxynaphth-1-yl)ethyl]butyramide

| | |
|---|---|
| N-[2-(7-methoxynaphth-1-yl)ethyl]butyramide | 50 g |
| Wheat starch | 15 g |
| Corn starch | 15 g |
| Lactose | 15 g |
| Magnesium stearate | 2 g |
| Silica | 1 g |
| Hydroxypropylcellulose | 2 g |

We claim:

1. A compound selected from those of general formula (I):

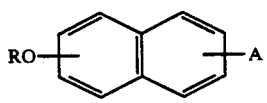

in which:

A represents a

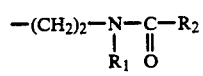

group,

R represents linear or branched lower alkyl, $R_1$ represents hydrogen or linear or branched lower alkyl, and $R_2$ represents heteroaryl or lower selected from pyridyl, thienyl, quinoxalyl, and indolyl, or a group of formula:

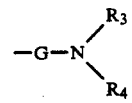

where G represents linear or branched lower alkyl, and $R_3$ and $R_4$ each form, with the nitrogen atom to which they are attached, a heterocyclic system selected from oxopyrrolidinyl, morpholinyl, oxopiperidinyl, piperazinyl, 4-(substituted phenyl)-piperazinyl, and 4-(substituted benzyl)piperazinyl. which it being understood that the term substituted $R_3$ means that the group is substituted by one to three inclusive radicals chosen from among lower alkyl, lower alkoxy, trifluoromethyl and halogen or R 1 forms with $R_2$ and the N-CO group a heterocyclic system of formula:

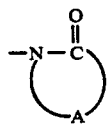

A being linear or branched alkyl having 2 to 8 carbon atoms, inclusive, and forming a ring having not more than six atoms. as well as, any isomers, epimers and diastereoisomers thereof and addition salts thereof with a pharmaceutically-acceptable acid, it being understood that the terms lower alkyl and lower alkoxy as used herein mean such as group comprising 1 to 6 carbon atoms.

2. The compound as claimed in claim 1, in which the OR group is in position 7, as well as any isomers, epimers and diastereoisomers thereof and addition salts thereof with a pharmaceutically-acceptable acid.

3. The compound as claimed in claim 1, in which $R_1$ represents a hydrogen atom or forms with $R_2$ and the N-CO group the system pyrrolidin-2-one, as well as any isomers, epimers and diastereoisomers, thereof and addition salts thereof pharmaceutically-acceptable acid.

4. A compound as claimed in claim 1, in which $R_2$ represents:
heteroaryl selected from 4-pyridyl, thienyl, 2-quinoxaline, and indolyl,
or a group of the formula:

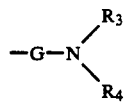

wherein G represents linear or branched lower alkylene, and $R_3$ and $R_4$ form, with the nitrogen atom to which they are attached, a heterocyclic system selected from:
2-oxopyrrolidinyl, morpholinyl, 2-oxopiperidinyl, 4-(4-fluorophenyl)piperazinyl, 4-(3-trifluoromethylphenylpiperazinyl, and 4-(2,3,4-trimethoxybenzyl)piperazinyl,
or $R_1$ forms with $R_2$ and the N-CO group a 2-oxopyrrolindinyl groups,
as well as isomers, epimers and diastereoisomers thereof, and addition salts thereof with a pharmaceutically-acceptable acid.

5. The compound as claimed in claim 1, which is N-[2-(7-methoxynaphth-1-yl)ethyl]-(2-oxopyrrolidin-1-yl)acetamide.

6. The compound as claimed in claim 1, which is N-[2-(7-methoxynaphth-1-yl)ethyl]pyrrolidin-2-one.

7. The compound as claimed in claim 1, which is N-[2-(7-methoxynaphth-1-yl)ethyl]-2-morpholinoacetamide.

8. The compound as claimed in claim 1, which is N-[2-(7-methoxynaphth-1-yl)ethyl]-2-{4-[(2,3,4-trimethoxyphenylmethyl]-piperazin-1-yl)acetamide, as well as its addition salts with a pharmaceutically-acceptable acid.

9. The compound as claimed in claim 1, which is N-[2-(7-methoxynaphth-1-yl)ethyl](indol-2-yl)carboxamide.

10. A pharmaceutical composition useful for treating melatoninergic system disorders containing as active principle an effective amount of at least one compound as claimed in claim 1 in combination with a pharmaceutically-acceptable excipient or vehicle.

11. A method for treating a living animal afflicted with disorder of the melatoninergic system comprising the step of administering to the said living animal an amount of a compound of claim 1 which is effective for the alleviation of the said condition.

* * * * *

UNITED STATES PATENT AND TRADEMARK OFFICE
CERTIFICATE OF CORRECTION

PATENT NO. : 5,194,614  Page 1 of 3

DATED : Mar. 16, 1993

INVENTOR(S) : Jean Andrieux, Raymond Houssin, Said Yous, Béatrice Guardiola, Daniel Lesieur It is certified that error appears in the above-indentified patent and that said Letters Patent is hereby corrected as shown below:

Column 1, approximately line 22; "70.44709describes" should read -- 70.44709 describes --.
Column 3, line 1; "and R" should read -- and $R_4$ --.
Column 5, line 15, 16; "ethyl 50 g bromoacetate" should read -- ethyl bromoacetate --.
Column 6, approximately line 17; ethyl]n" should read --ethyl]
Column 6, line 18; before "(7-Methoxynaphth-" insert --N[2- --.
Column 6, line 18; "]n-methylamine" should read -- ]N-methylamine --.
Column 6, line 22; after "Stage E" insert -- and directly reducing the amide so obtained. --. (2nd PA 8-23-91)
Column 6, line 35; "methoxyl-" should read -- methoxyl-1- --.
Column 7, approximately line 61; "-lyl)" should read -- -1-yl) --.
Column 8, line 5; "ethyl)-7-" should read --ethyl}-7- --.
Column 8, lines 16/17; move the "e" from the end of line 16 to the beginning of line 17 and insert before "thylamine".
Column 8, line 37; "4chlorobutyramide" should read -- 4-chlorobutyramide --.
Column 9, lines 24/25; move the "e" from the end of line 24 to the beginning of line 25 and insert before "thyl".
Column 9, line 32; "maonetic" should read -- magnetic --.
Column 9, line 50; "$CDCl_3$" should read -- $CDCl_3$: --.
Column 9, line 61; "maonetic" should read -- magnetic --.
Column 10, line 2; insert a colon ":" after "$CDCl_3$".
Column 11, lines 40, 41; move the closing parenthesis ")" from the beginning of line 41 to the end of line 40 and insert before the hyphen "-".
Column 11, line 51; "-lyl)" should read -- -1-yl) -- .
Column 12, approximately line 13; "piperazin-1-1] " should read -- piperazin-1-yl] --.
Column 12, line 43; "maonetic" should read -- magnetic --.

UNITED STATES PATENT AND TRADEMARK OFFICE
CERTIFICATE OF CORRECTION

PATENT NO. : 5,194,614            Page 2 of 3

DATED : Mar. 16, 1993

INVENTOR(S) : Jean Andrieux, Raymond Houssin, Said Yous, Béatrice Guardiola, Daniel Lesieur It is certified that error appears in the above-indentified patent and that said Letters Patent is hereby corrected as shown below:

Column 13, approximately line 17; begin a new line with "Melting".
Column 13, line 62; "[(2,3,4TRIMETHOXY-" should read -- [(2,3,4-TRIMETHOXY- --.
Column 14, line 2; "4TRIMETHOXY-" should read -- -- 4-TRIMETHOXY- --.
Column 14, lines 5, 6, and 12; in each instance (3), move the "e" at the end of the line to the beginning of the next line and insert before "thylamine,".
Column 14, line 14 and 15; move the closing bracket "]" from the beginning of line 15 to the end of line 14 and insert before the hyphen.
Column 14, lines 19 and 20; move the closing bracket "]" from the beginning of line 20 to the end of line 19 and insert before the hyphen.
Column 14, line 27; "-2YL" should read -- -2-2YL --.
Column 15, line 14, 15; move the "I" from the end of line 14 to the begining of line 15 and insert before "ODOACETAMIDE".
Column 15, line 20; "YL   ETHYL]" should read -- YL)ETHYL --.
Column 18, line 8; move the "1" at the beginning of line 8 to the end of line 7 and insert before the hyphen "-".
Column 18, approximately line 18; "of general for-" should read -- of the for- --. (PA 2-25-91, P. 1)
Column 18, line 39; delete "or". (R&A 6-23-92, P. 1)
Column 18, line 39; delete "lower". (R&A 12-11-91, P.1)
Column 18, line 49; delete "each". (R&A 12-11-91, P.2)
Column 18, line 54; delete "which". (R&A 6-23-92, P. 1)
Column 18, line 57; "trifluoromethyl and" should read -- trifluoromethyl, and --. (PA 2-25-91, P. 2)
Column 18, line 67; insert "with" before "A".
Column 19, approximately line 5; "mean such as" should read -- mean such a --. (PA 2-25-91, P. 3)

UNITED STATES PATENT AND TRADEMARK OFFICE
CERTIFICATE OF CORRECTION

PATENT NO. : 5,194,614                    Page 3 of 3
DATED      : Mar. 16, 1993
INVENTOR(S): Jean Andrieux, Raymond Houssin, Said Yous, Béatrice Guardiola, Daniel Lesieur It is certified that error appears in the above-indentified patent and that said Letters Patent is hereby corrected as shown below:

```
Column 19, line 6; "group comprising 1" should read
     -- group having 1 --. (R&A 12-11-91, P. 2) (Cl. 1)
Column 19, line 6; "atoms." should read -- atoms, inclusive. --.
     (R&A 12-11-91, P. 2, ln. 8) (Cl.1)
Column 19, line 7; "The compound" should read -- A compound --.
     (R&A  12-11-91, P. 2, ln. 11) (Cl. 2)
Column 19, line 16; "thereof pharmaceutically-acceptable"
     should read --thereof, with a pharmaceutically-acceptable--
     (R&A 12-11-91, P. 2) (Cl. 3)
Column 19, line 30; "alkylene," should read --alkyl,--.
     (Cl. 4, old Cl. 27, R&A 6-23-92, P.2)
Column 20, line 4, "rolindinyl" should read -- rolidinyl --.
     (Cl. 4, old Cl. 27, R&A 6-23-92, P. 2)
Column 20, line 18; "-1-yl)" should read -- -1-yl --.
     (Cl. 8, old Cl. 16)
Column 20, line 30; "with disorder" should read
     -- with a disorder --. (Cl. 11, old Cl. 26 -
     R&A 2-25-91, P. 6)
```

Signed and Sealed this

Nineteenth Day of April, 1994

Attest:

BRUCE LEHMAN

Attesting Officer          Commissioner of Patents and Trademarks

UNITED STATES PATENT AND TRADEMARK OFFICE
CERTIFICATE OF CORRECTION

PATENT NO. : 5,194,614

DATED : March 16, 1993

INVENTOR(S) : Jean Andrieux, Raymond Houssin, Said Yous, Béatrice Guardiola and Daniel Lesieur It is certified that error appears in the above-indentified patent and that said Letters Patent is hereby corrected as shown below:

Col. 17, line 50; "6.3 X $10^{11}$," should read -- 6.3 X $10^{-11}$, --.

Signed and Sealed this

Seventh Day of June, 1994

Attest:

BRUCE LEHMAN

Attesting Officer

Commissioner of Patents and Trademarks